United States Patent [19]

Spranger et al.

[11] Patent Number: 4,994,055

[45] Date of Patent: Feb. 19, 1991

[54] FLUID FLOW CONTROL APPARATUS

[75] Inventors: Douglas M. Spranger; Karl D. Kirk, III, both of New York, N.Y.; Robert Cohen, Duxbury; Preston J. Keeler, III, Westport, both of Mass.; Jeffrey A. Stein, Milford, Conn.

[73] Assignee: Pfizer Hospital Products Group, Inc., New York, N.Y.

[21] Appl. No.: 330,399

[22] Filed: Mar. 29, 1989

[51] Int. Cl.[5] .................. A61B 19/00; B67D 5/08; B67D 5/14

[52] U.S. Cl. .................. 604/403; 604/247; 604/255; 137/399; 222/67; 222/448; 222/517

[58] Field of Search ........ 604/247, 122, 127, 254–256, 604/403, 407; 222/67, 448, 450, 517; 137/399

[56] References Cited

U.S. PATENT DOCUMENTS 3,216,419 11/1965 Scislowicz .................. 137/399
3,896,733 7/1975 Rosenberg .
4,030,516 6/1977 Foller .................. 137/399

Primary Examiner—Stephen C. Pellegrino
Attorney, Agent, or Firm—Peter C. Richardson; Lawrence D. Akers; John L. LaPierre

[57] ABSTRACT

A reservoir outlet control device for controlling fluid flow from a reservoir. The device is particularly suitable for controlling fluid outflow from a blood collecting and blood delivery reservoir.

28 Claims, 5 Drawing Sheets

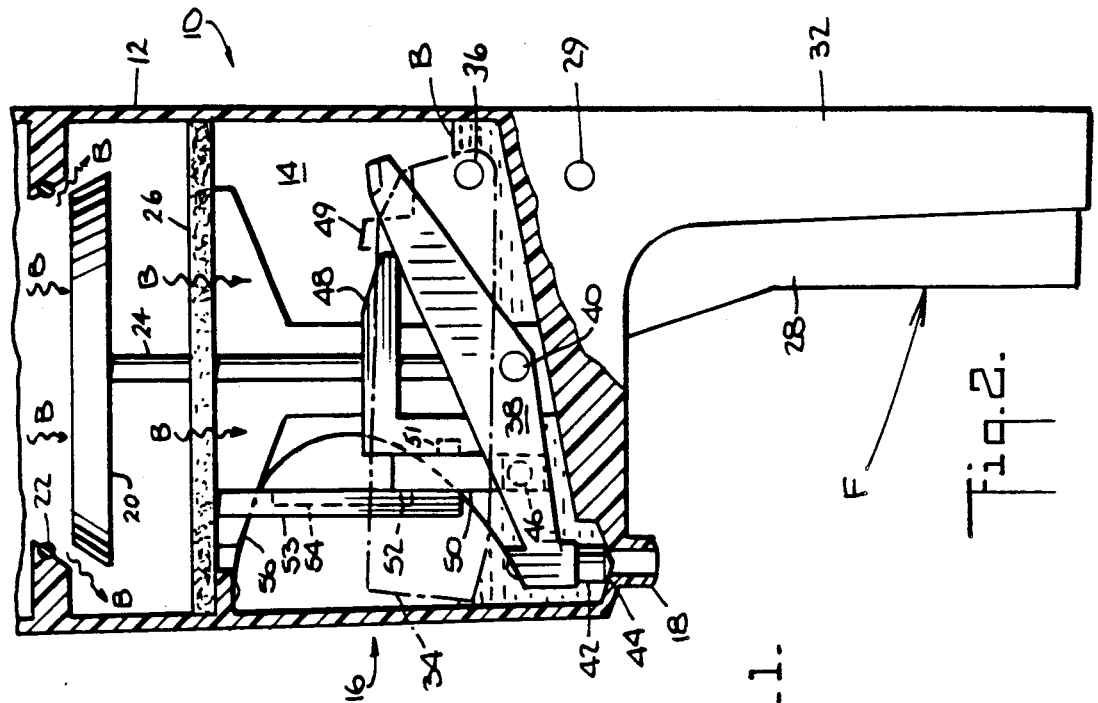
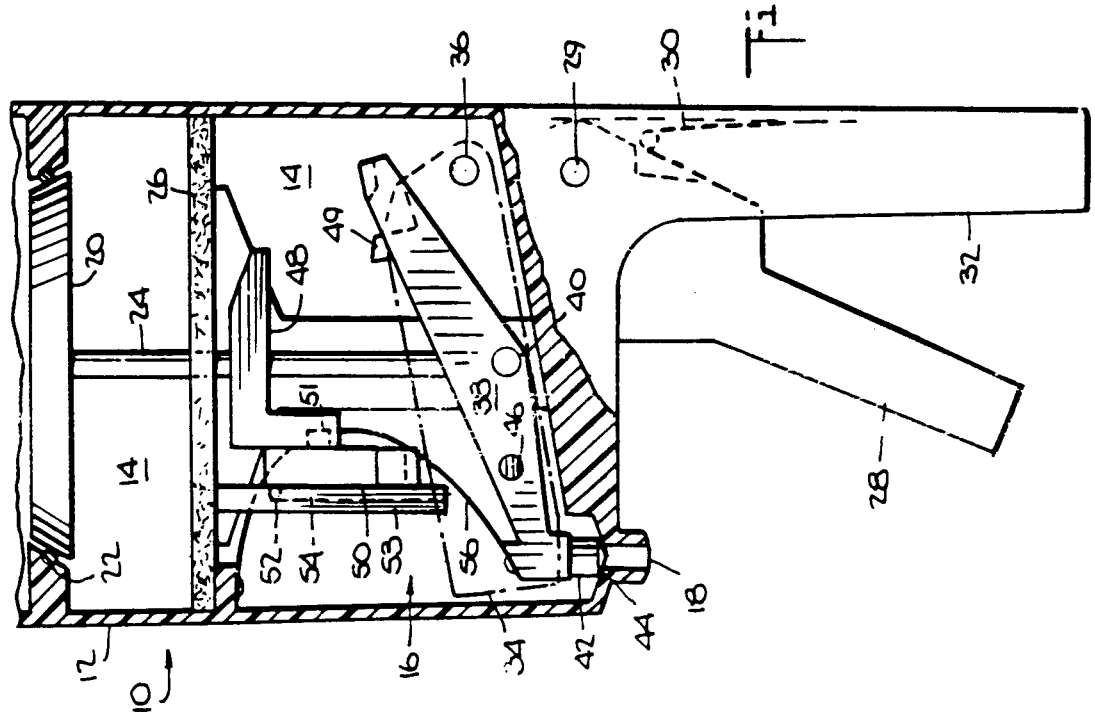

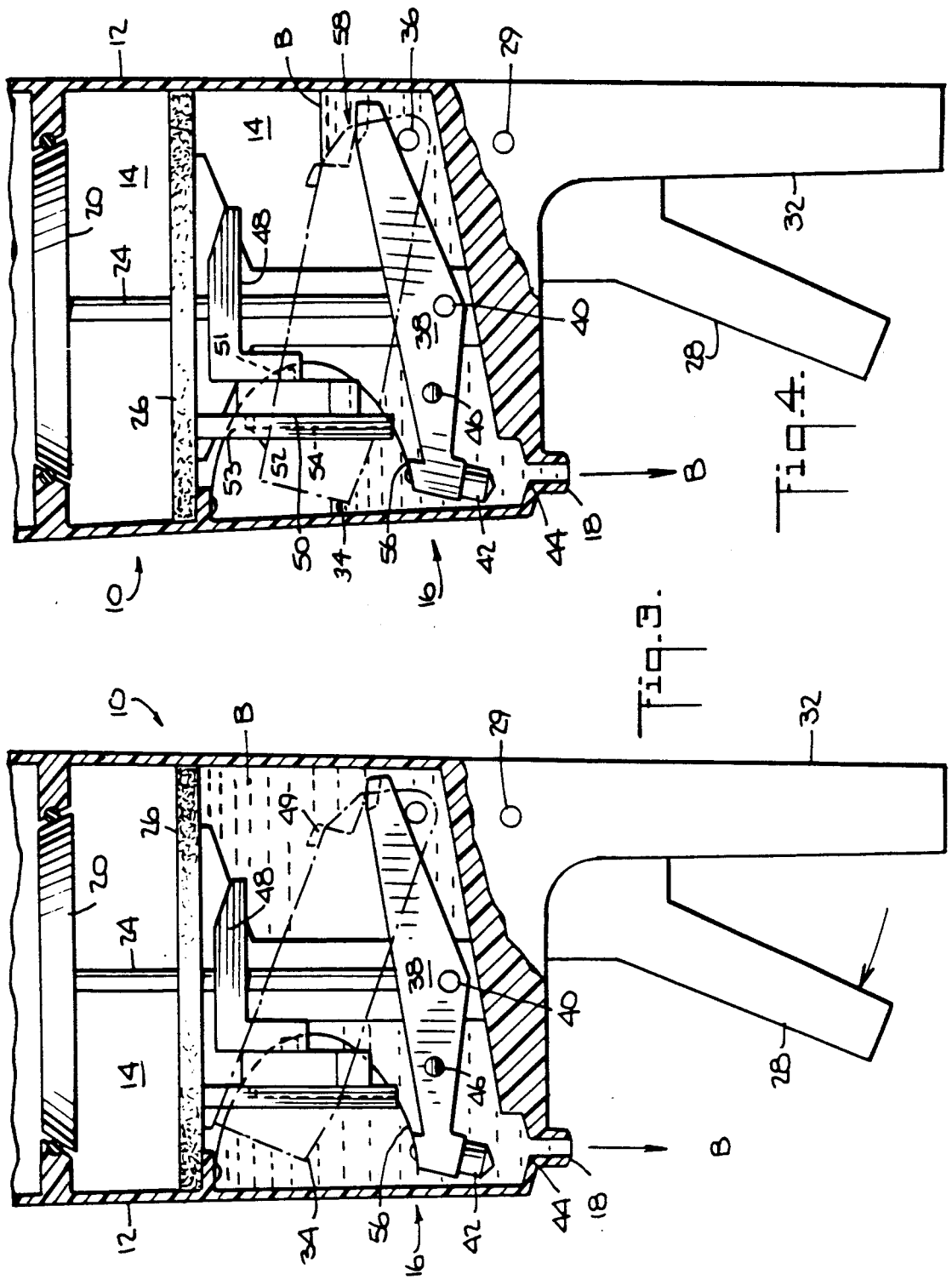

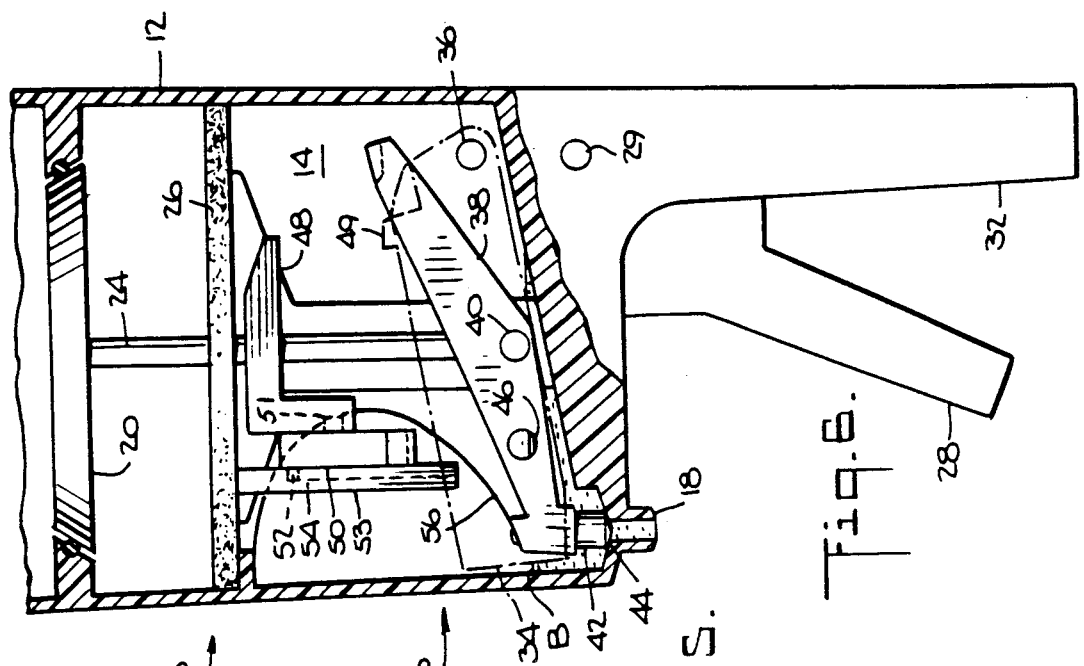
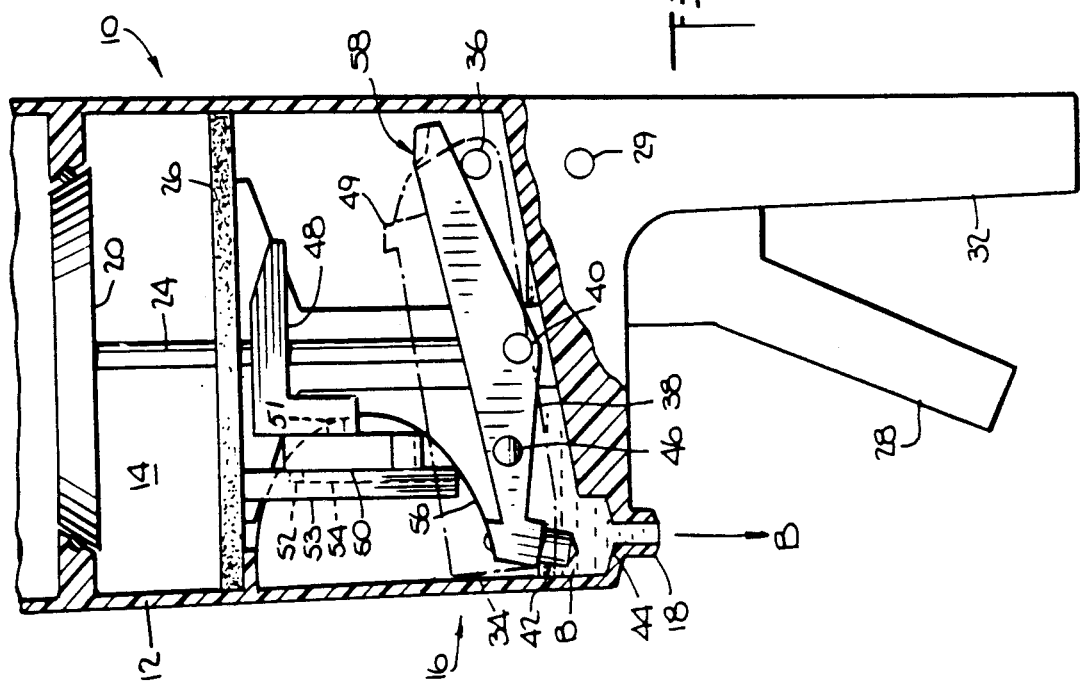

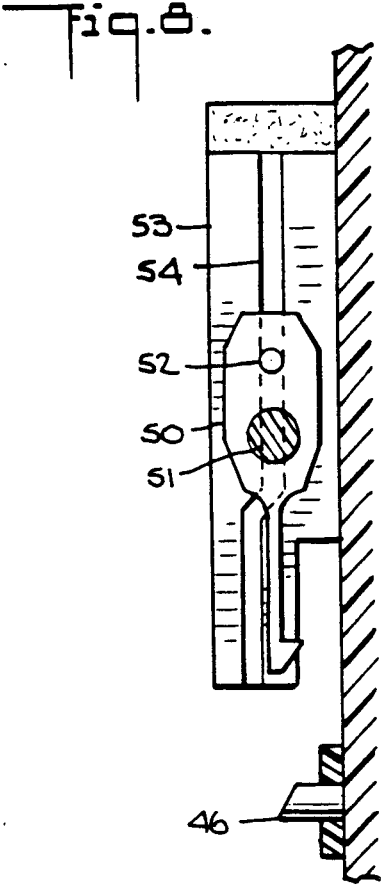
Fig. 8.
Fig. 9.
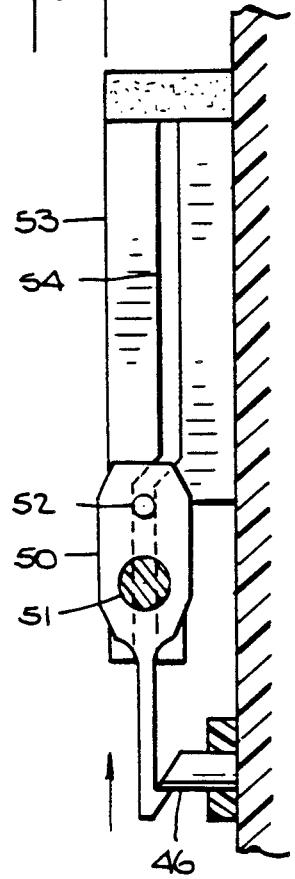
Fig. 10.
Fig. 11.
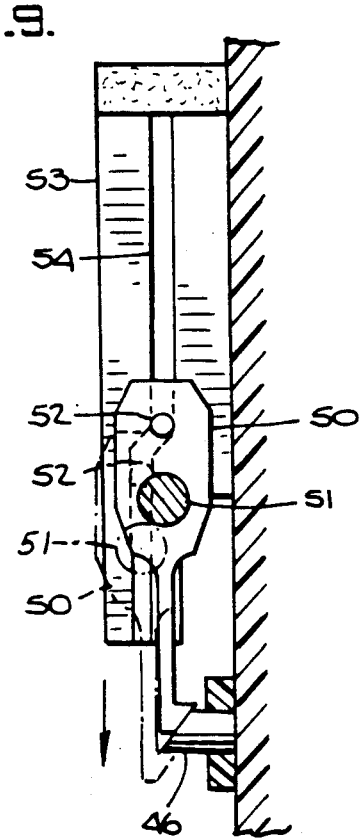
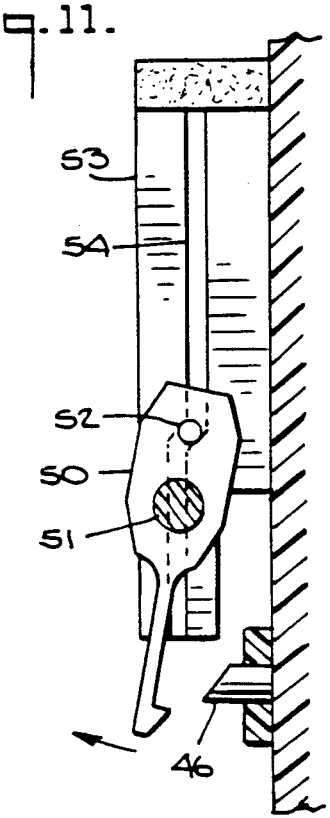

4,994,055

FLUID FLOW CONTROL APPARATUS

BACKGROUND OF THE INVENTION

The present invention relates generally to fluid flow control and, more particularly it relates to a device for controlling the flow of fluid out of a fluid collection reservoir. The device is especially suitable for use in the control of the outflow of blood from a blood collection and transfer reservoir.

There have been introduced into the marketplace a number of direct whole blood cardiotomy reservoirs and methods for using reservoirs during the recovery and collection of blood for subsequent return to a patient. Typically, a system might utilize a negative pressure source for blood delivery and collection in a reservoir and use the force of gravity for return of the collected blood to the patient. Alternatively, instead of using gravity for blood return, for example, a roller pump or an intravenous pump might be used for reinfusion of collected blood to increase the rate of blood return to the patient. Another technique might be the delivery (under positive pressure) to the patient of blood previously collected from the patient or delivery (also under positive pressure) to the patient of donor blood. In each system, extreme caution must be exercised to prevent the inroduction of air into the patient return or delivery line, the presence of which could create an air embolism endangering the patient.

Disclosure of a blood collection and delivery apparatus can be found in U.S. Pat. No. 3,896,733. In this device, there is employed in each of two blood collection chambers a float valve which moves with the level of blood fluid in the chamber. The operation of the float valve is governed solely by the rise and fall of the level of blood in the chamber. Specifically, when the fluid in the chamber drops to the level of the valve seat at the bottom of the chamber, the valve sinks into sealing engagement with the valve seat to close off the fluid outlet from the chamber. The valve, which takes the form of a floating disc, is designed to prevent air from entering the chamber outlet. When fluid is again introduced into the chamber, the float valve is designed to rise with the rising fluid level.

A primary disadvantage of the aforementioned fluid outflow control system is that, should the floating disc not be properly seated, then air could enter the chamber outlet line leading to the patient. Improper seating could result should the floating disc become tilted or askew, for example, perhaps resulting from material buildup on the valve seat, material buildup on the blood surface or material buildup along the chamber wall. Coagulating blood could also cause disc tilting and result in an improper outlet seal. Due to the complex nature and makeup of blood, one or more of these undesirable situations could occur and result in air passage into the patient line, particularly when the floating valve depends solely upon the fluid level and incorporates no additional feature to positively urge the valve into sealing engagement with the valve seat.

The primary objective of the present invention is to advance the art field by providing a reliable reservoir fluid outlet control device, particularly a device suitable for controlling blood outflow from a blood collection reservoir, for releasably sealing the reservoir outlet against fluid passage therethrough. Accordingly, herein disclosed is a reservoir outlet control device which is especially designed and configured to provide a positive force for urging the outlet control device into a fluid sealing position at a predetermined fluid level in the reservoir and for preventing air entry into the patient delivery line.

SUMMARY OF THE INVENTION

The present invention is directed toward a reservoir outlet control device for controlling fluid flow from a reservoir outlet port comprising a member being movable responsive to a level of fluid in the reservoir, means for releasably sealing the outlet port against fluid flow, means for releasing the outlet port seal, and means for first maintaining an open outlet port above a predetermined level of fluid in the reservoir and then for reestablishing the outlet port seal. The device might further include biasing means for urging the sealing means toward a reservoir outlet port sealing position. The reservoir fluid might be blood, might at least be partially blood, or might be any liquid for delivery to a living body. Furthermore, the fluid leaving the reservoir might be pressurized. The member might be a float and the sealing means might further include an arm. The sealing means might comprise a self aligning seal which could take the form of a cup-shaped suction disc. In one embodiment, the arm might be a resilient member. In another embodiment, the arm might further include means for preventing movement of the arm when the fluid in the reservoir is below a predetermined level.

Also included to be within the scope of the invention, in one embodiment, is an outlet control device for controlling the flow of blood from a blood collecting and delivery reservoir comprising float means being movable responsive to a level of blood in the reservoir, lever means including means for sealing the reservoir outlet against blood flow therethrough, means for displacing the lever means to a position releasing the reservoir outlet seal, and means for holding the lever means in the seal releasing position until a predetermined level of blood remains in the reservoir and thereafter freeing the lever means for reestablishing the outlet seal. The lever means might be a resilient member. The float means and the lever means cooperatively engage one another until the predetermined level of blood remains in the reservoir, below which level, the float means and the lever means disengage to restore the seal. The device might further include means for preventing displacement of the lever means when the blood is below the predetermined level. The device further includes means for activating the lever displacing means and means for returning the lever displacing means to a preactivating position. The lever displacing means might be a pawl adapted to engage a tab on the lever means. Additionally, there might be included means for guiding the movement of the pawl and means for disengaging the pawl and the tab. The blood leaving the reservoir might be pressurized and the sealing means might comprise a self aligning seal, such as a cup-shaped suction disc. Lastly, the device might further include biasing means for urging the lever means toward a reservoir outlet sealing position.

The invention further embodies a blood collection reservoir comprising a housing having an inlet, a collection chamber and an outlet, and means for controlling the flow of blood through the outlet, the flow control means comprising float means being movable responsive to a level of blood in the reservoir, lever means including means for sealing the reservoir outlet against blood flow therethrough, means for displacing the lever means to a position releasing the reservoir outlet seal, and means for holding the lever means in the seal releasing position until a predetermined level of blood remains in the reservoir and thereafter freeing the lever means for reestablishing the outlet seal. The lever means might preferably be a resilient member. The reservoir might further include biasing means for urging the lever means toward a reservoir outlet sealing position.

BRIEF DESCRIPTION OF THE DRAWINGS

FIG. 1 is a partial sectional view of a blood collection reservoir illustrating, in accordance with the principles of the present invention, structural detail of the reservoir blood outlet section and blood flow control device in an inoperative or at rest position with the port closed and before the introduction of blood to the outlet port area.

FIGS. 2-5 are views similar to the view depicted in FIG. 1 but sequentially showing the control device in operation with the introduction of blood to the outlet port (FIG. 2) and the flow of blood through the outlet port (FIGS. 3-5).

FIG. 6 is a view substantially as shown in FIG. 1 but with a level of blood remaining above the reservoir outlet port after the flow of blood therethrough and after the outlet port has been sealed.

FIG. 7 is a view similar to FIG. 4 and depicts another embodiment of the reservoir blood outlet control device.

FIGS. 8-11 schematically depict enlarged views of the operation of the structure designed to open the outlet port seal.

DETAILED DESCRIPTION OF THE PREFERRED EMBODIMENTS

Figure 2:
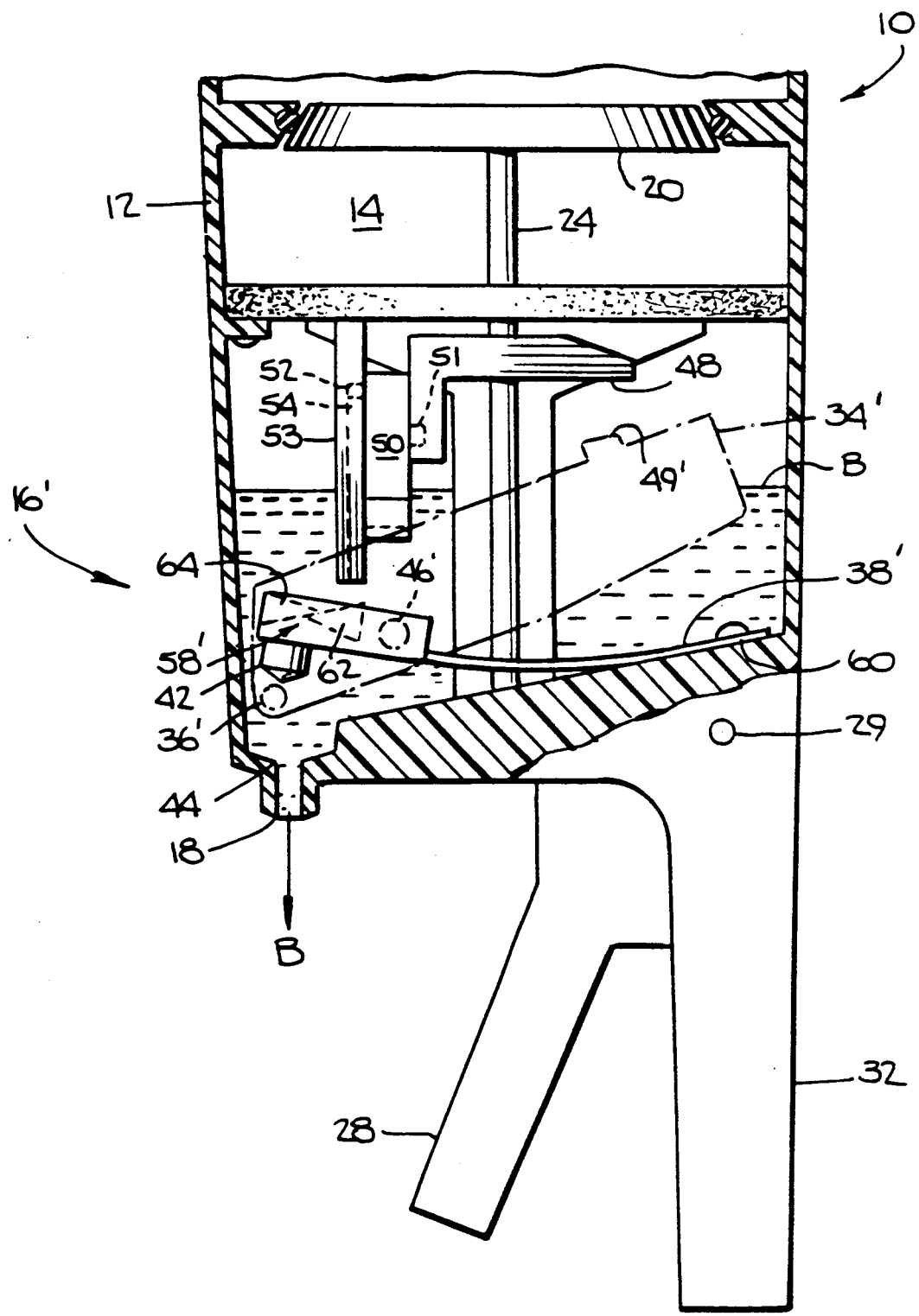

The description herein presented refers to the accompanying drawings in which like reference numerals refer to like parts throughout the several views. First, turning to FIG. 1, there is illustrated a partial sectional view of a multicompartmental blood collection reservoir 10 having housing wall 12, blood transfer chamber 14 and an outlet control device generally designated as 16. Reservoir 10 is shown as it would appear prior to usage. There is a compartment above chamber 14 from whence collected blood is transferred to chamber 14. It should be understood that, while the term blood is herein used, the collected fluid could, for example, be substantially whole blood or at least partially whole blood. Furthermore, the fluid could include saline, irrigation fluid, heparin or other fluids associated with surgical procedures. The fluids which leave the reservoir are suitable for ultimate delivery to a living body. It should be understood that, while a multicompartmental blood collection reservoir will be described, a reservoir having one compartment would be suitable for the collection of blood and other fluids. Likewise, reservoir 10 is suitable for handling fluids other than blood. Reservoir 10 further includes outlet 18, valve 20, seal ring 22, rod 24, blood filter 26, trigger 28, spring 30 and handle 32. Trigger 28 is pivotally connected to reservoir 10 by pin 29 and further engages rod 24 at a location not herein shown. A compression spring or the like (not shown) could be used in place of the spring configuration designated 30. The spring is designed to return trigger 28 to its preactivation position.

Outlet control device 16 has a number of interrelated components. A first component is float 34 which is pivotally connected to the reservoir by pin 36. The next component is lever 38 which is pivotally connected to the reservoir by pin 40, with lever 38 including valve 42 configured to engage outlet 18 to seal the outlet at a valve seat generally designated as 44. Lever 38 further includes projecting post or tab 46. Another component includes actuator 48, which is connected to rod 24, with the actuator further engaging pawl 50 via pin 51. A pin 52 connects pawl 50, with pin 52 shown as being located in member 53 having slot 54, and it is the cooperative action of pin 52 and slot 54 which guides the movement of the pawl. Lastly, there is spring 56 which engages lever 38 to bias the lever toward a reservoir outlet sealing position. Float 34 further includes a surface 49 which, in FIG. 1, is shown positioned to stop the downward movement of actuator 48. Surface 49 is designed to obstruct a continued movement of actuator 48 when the surface and actuator engage one another. Thus, without a predetermined level of fluid in reservoir chamber 14, the outlet seal cannot be inadvertently broken.

Turning now to FIGS. 2 through 5, there are shown, sequentially, views of the reservoir and outlet control device in operation. A person, placing handle 32 in the palm of a hand and with fingers extending around trigger 28, could exert a force F on trigger 28 and cause displacement of the trigger as shown in FIG. 2. This displacement of trigger 28, pivoting about pin 29, causes compression of spring 30 (not shown in this view) and the downward movement of rod 24, valve 20, actuator 48 and pawl 50. As the seal between valve 20 and seal ring 22 is broken, blood B (or other fluid) is allowed to enter chamber 14 from a compartment above chamber 14 where blood had previously been collected. The blood being collected in chamber 14 rises and causes float 34 to rotate and rise accordingly. The rotation of float 34 causes surface 49 to rotate to a position wherein surface 49 will no longer obstruct the downward movement of actuator 48. There is now a clearance between the rightmost end portion of actuator 48 and surface 49. Pawl 50 engages tab 46 on lever 38 but, in this view, as yet the lever remains stationary. Outlet 18 remains sealed as valve 42 remains seated on valve seat 44. Spring 56 biases lever 38 and valve 42 toward an outlet closing position. No blood flows through outlet 18. Valve 42 is herein shown as a stopper but, preferably, it could take the configuration of a cup-shaped suction disc which would present a seal having a self aligning feature.

Turning next to FIG. 3, upon release of force F compressed spring 30 (not shown) urges trigger 28, rod 24, valve 20, actuator 38 and pawl 50 to return their original positions shown in FIG. 1. The seal between valve 20 and seal ring 22 has been reestablished to block the further inflow of blood into chamber 14. Float 34 has further risen as the level of blood in chamber 14 has increased. Also the seal between valve 42 and seat 44 has been broken to allow blood to flow out of chamber 14 through outlet 18 for delivery to a patient or to another storage compartment. The upward movement of actuator 48 and pawl 50, the pawl having been engaged with tab 46 as shown in FIG. 2, first causes the upward displacement of lever 38, as the lever pivots about pin 40, resulting in the unsealing of outlet 18. Thereafter, pawl 50 and tab 46 disengage and lever 38, being biased by spring 56, attempts to return valve 42 to seat 44 to close outlet 18. (The operation of pawl 50 and lever 38 is shown in greater detail in FIGS. 8-11). However, float 34 and lever 38, at end location generally designated as 58, cooperatively engage one another to prevent lever 38 from returning to its outlet sealing position. Float 34, being bouyed by the level of blood in chamber 14, resists the counterclockwise movement of lever 38 at contact location 58 and the outlet remains open allowing passage of blood therethrough. Although not shown in these views, transfer chamber 14 could be pressurized so that the fluid leaving outlet port 18 is under a pressure above atmospheric. A port could be established in wall 12 and, for example, a sphygmomanometer bulb, a pressure gauge and tubing communicating with the port could be used to establish desired pressure levels.

Next, we turn to FIG. 4 and observe that outlet 18 remains open to blood outflow, the level of blood in chamber 14 has dropped, float 34 has rotated counterclockwise responsive to the lowered blood level and that float 34 and lever 38 remain in contact at location 58 thus preventing the return of valve 42 to seat 44. FIG. 5 shows yet the further lowering of the blood level in chamber 14 and that float 34 and lever 38 remain in engagement at location 58 to keep outlet 18 open. It should be observed that contact between the float and lever at location 58 is about to be broken. Lastly, we turn to FIG. 6 and observe that there is no longer contact between float 34 and lever 38 at location 58 and that lever 38, being biased by spring 56, has further rotated to return valve 42 to seat 44 to thereby seal outlet 18 against further blood outflow. It should be observed that a level of blood remains above the closed outlet port to insure that no air is allowed to pass through outlet 18. The sequences depicted in FIGS. 2 through 6 can now be repeated.

FIG. 7 shows yet another embodiment of outlet control device 16. Here the outlet control device has been designated 16', the float 34', the float pivot pin 36', the lever 38', the tab 46', the surface for obstructing movement of actuator 48 has been designated 49', and the location wherein float 34' and lever 38' engage has been designated 58'. Lever 38' is a resilient member, perhaps a leaf spring or the like, connected to the reservoir by rivet 60. Operation of outlet control device 16' is substantially as hereinbefore described with respect to device 16. Movement of actuator 48 and pawl 50 to engage tab 46' and open outlet port 18 and raise lever 38' has been completed. Here as the level of blood B drops, float 34' rotates in a clockwise direction about pivot 36'. At location 58', triangulated section 62 of float 34' and triangulated section 64 of resilient member 38' are slidingly engaged to maintain outlet port 18 open, that is, lever 38' is releasably held in the position down. As float 34' continues its clockwise rotation as the blood level drops, sections 62 and 64 will slide past one another and lever 38', released from its raised position, will move downwardly and valve 42 will engage valve seat 44 to seal outlet port 18 against further blood outflow. As before, a level of fluid will remain above closed outlet port 18. Thereafter, the fill and discharge cycle of transfer chamber 14 can begin anew.

FIGS. 8-11 schematically show the operation of the pawl as it is used to engage and displace the lever arm. The line of sight is looking basically at the pawl from right to left. FIG. 8 shows pawl 50 substantially in the position of FIG. 1, that is, at least prior to activation of the pawl. The downward and outward movement of pawl 50 will be governed by movement of pin 52 traveling along slot 54. FIG. 9 shows the pawl just prior to engagement with tab 46 and shows, in phantom, the pawl in latching engagement with tab 46 (as shown in FIG. 2). In FIG. 10, pawl 50 is in engagement with tab 46 and is about to move upwardly. Upward movement of pawl 50 latched to tab 46 will cause upward displacement of lever arm 38 and the opening of outlet port 18. FIG. 11 shows the rocking motion of pawl 50 and the release of tab 46. Lever 38 will basically be in the position shown in FIG. 3. Pawl 50 will continue moving upwardly to return to the position shown in any of FIGS. 1 and 3-8.

The present invention has been described herein with specific reference to the preferred embodiments thereof. However, those skilled in the art will understand that changes may be made in the form of the invention covered by the claims without departing from the scope and spirit thereof, and that certain features of the invention may sometimes be used to an advantage without corresponding use of the other features.

What is claimed is:

1. A reservoir outlet control device for controlling fluid flow from a reservoir comprising a fluid containment chamber, containing collected fluid, having an outlet port and including a member being movable responsive to a level of fluid in said chamber, lever means including sealing means for releasably sealing said outlet port against fluid flow therethrough, means coacting with said lever means for releasing said outlet port seal, and means for releasably latching said member and said lever means for first maintaining an open outlet port allowing fluid flow therethrough until a predetermined level of fluid remains in said chamber and then for reestablishing said outlet port seal.

2. The device according to claim 1 wherein said fluid is at least partially blood.

3. The device according to claim 1 further including biasing means for urging said sealing means toward a reservoir outlet port sealing position.

4. A reservoir outlet control device for controlling fluid outflow from a reservoir comprising a housing, adapted to contain collected fluid, having an outlet, a float being movable responsive to a level of fluid in said housing, an arm including means for sealing said outlet against fluid outflow, means cooperating with said arm for moving said arm to a position releasing said outlet seal, and means for releasably latching said float and said arm for first maintaining said released outlet seal until a predetermined level of fluid remains in the reservoir and thereafter for restoring said outlet seal.

5. The device according to claim 4 wherein said arm comprises a resilient member.

6. The device according to claim 4 wherein said fluid comprises a liquid for delivery to a living body.

7. The device according to claim 6 wherein said fluid is at least partially blood.

8. The device according to claim 4 further including biasing means for urging said arm toward a reservoir outlet sealing position.

9. The device according to claim 4 further including means for pressurizing said fluid leaving said reservoir.

10. The device according to claim 4 further including means for preventing movement of said arm when said fluid is below said predetermined level.

11. The device according to claim 4 wherein said sealing means comprises a self aligning seal.

12. The device according to claim 11 wherein said sealing means is a cup-shaped suction disc.

13. An outlet control device for controlling the flow of blood from a blood collecting and delivery reservoir comprising a housing having an outlet and including blood collected therein, said housing further including float means being movable responsive to a level of blood in said housing, lever means including means for sealing said outlet against blood flow therethrough, means for displacing said lever means to a position releasing said outlet seal, and means for releasably latching said lever means and said float means for holding said lever means in said seal releasing position until a predetermined level of blood remains in the reservoir and thereafter freeing said lever means for reestablishing said outlet seal.

14. The device according to claim 13 wherein said lever means comprises a resilient member.

15. The device according to claim 13 wherein said holding means comprises said float means and said lever means being disposed in cooperative engagement with one another until said predetermined level of blood remains in the reservoir, below which level, the float means and the lever means disengage to restore the seal.

16. The device according to claim 13 further including means for preventing displacement of said lever means when said blood is below said predetermined level.

17. The device according to claim 13 further including means for activating said lever displacing means.

18. The device according to claim 17 further including means for returning said lever displacing means to a preactivating position.

19. The device according to claim 18 wherein said lever displacing means comprises a pawl adapted to engage a tab disposed on said lever means.

20. The device according to claim 19 further including means for guiding the movement of said pawl.

21. The device according to claim 20 wherein said guiding means includes means for disengaging said pawl and said tab.

22. The device according to claim 13 further including biasing means for urging said lever means toward a reservoir outlet sealing position.

23. The device according to claim 13 further including means for pressurizing said blood leaving said reservoir.

24. The device according to claim 13 wherein said sealing means comprises a self aligning seal.

25. The device according to claim 24 wherein said sealing means is a cup-shaped suction disc.

26. A blood collection reservoir comprising a housing having an inlet, a collection chamber and an outlet, and means for controlling the flow of blood through said outlet, said collection chamber including float means being movable responsive to a level of blood in said chamber, first sealing means for releasably sealing said inlet to control the flow of blood into the chamber, means for selectively regulating the operation of said first sealing means, lever means including means for releasably sealing said outlet against blood flow therethrough, means coacting with said lever means for displacing said lever means to a position releasing said outlet seal, and means for releasably latching said float means and said lever means for holding said lever means in said outlet seal releasing position until a predetermined level of blood remains in the collection chamber and thereafter freeing said lever means for reestablishing said outlet seal.

27. The reservoir according to claim 26 wherein said lever means comprises a resilient member.

28. The reservoir according to claim 26 further including biasing means for urging said lever means toward a reservoir outlet sealing position.

* * * * *